United States Patent [19]

Miyamura et al.

[11] 4,182,894

[45] Jan. 8, 1980

[54] CONTINUOUS PROCESS FOR THE PREPARATION OF IMIDAZOLINE COMPOUNDS

[75] Inventors: Akio Miyamura, Funabashi; Yukio Kusumi, Chiba; Naoichi Omoto, Tokyo, all of Japan

[73] Assignee: The Lion Fat and Oil Co., Ltd., Tokyo, Japan

[21] Appl. No.: 879,931

[22] Filed: Feb. 22, 1978

[30] Foreign Application Priority Data

Mar. 8, 1977 [JP] Japan .................................. 52-25219

[51] Int. Cl.$^2$ .......................................... C07F 233/14
[52] U.S. Cl. ................................................ 548/352
[58] Field of Search ........................................ 548/352

[56] References Cited

U.S. PATENT DOCUMENTS

| | | | |
|---|---|---|---|
| 2,528,379 | 10/1950 | Mannheimer | 548/352 |
| 2,892,812 | 6/1959 | Helbing | 560/94 |
| 3,408,361 | 10/1968 | Mannheimer | 548/352 |

FOREIGN PATENT DOCUMENTS

| | | | |
|---|---|---|---|
| 904446 | 8/1962 | United Kingdom | 560/94 |
| 950535 | 2/1964 | United Kingdom | 560/94 |

*Primary Examiner*—Richard Raymond
*Attorney, Agent, or Firm*—Sprung, Felfe, Horn, Lynch & Kramer

[57] ABSTRACT

An improved continuous process for the synthetic preparation of imidazoline compounds is provided by the invention in which a mixture of an N-alkylol-substituted ethylenediamine and a higher fatty acid is supplied contiuously to the upper part of a packed reaction column kept at 180° to 250° C. under a reduced pressure of 40 to 70 mmHg while the water formed by the condensation reaction is distilled out in parallel with the refluxing of the diamine and the reaction mixture, having stayed for at least 10 minutes in the reaction zone, is continuously discharged from the reservoir vessel installed below the reaction column to give the objective compound in a high yield.

4 Claims, 1 Drawing Figure

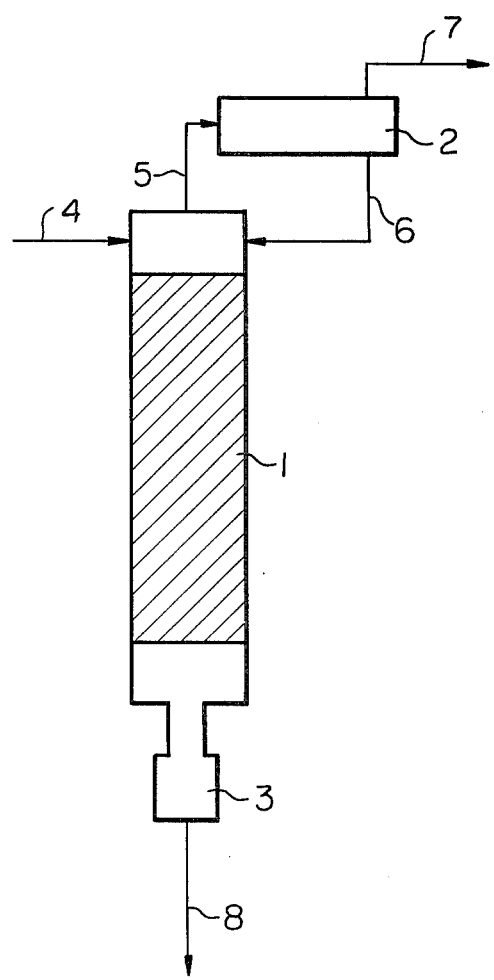

CONTINUOUS PROCESS FOR THE PREPARATION OF IMIDAZOLINE COMPOUNDS

BACKGROUND OF THE INVENTION

The present invention relates to a continuous process for the preparation of high-quality imidazoline compounds by the reaction of a diamine and a higher fatty acid.

Imidazoline is a compound insoluble in water but dispersible in water giving a homogeneous aqueous dispersion exhibiting excellent foaming. On the other side, derivatives of imidazoline are generally soluble in water and their aqueous solution is useful as an amphoteric surface active agent exhibiting excellent detergency and foaming with an advantage of very low irritation to human skins. Therefore they can find very wide applications as a detergent ingredient in shampoo and various kinds of detergents for kitchen and laundry use as well as an emulsifying agent or a basic ingredient in cosmetics. Thus the demand for these imidazoline compounds is rapidly growing and an effective method for the preparation of these compounds with high quality is earnestly desired.

In the prior art, several methods are proposed for the preparation of the imidazoline compounds by the reaction of a diamine and a higher fatty acid. See, for example, British Pat. No. 985,321 and U.S. Pat. No. 3,408,361. The method disclosed in the former reference, in which the starting reactants are brought into reaction under agitation in a vessel with introduction of nitrogen gas while the distillate is continuously removed out of the vessel, is, however, defective due to the very low maximum yield of the desired product.

In the method disclosed in the latter reference, the reaction is carried out in a vessel, of which the temperature and the pressure are gradually changed, with continuous addition of the diamine at a rate to compensate the amount distilling out of the vessel taking several hours to complete the reaction. This method is advantageous by the high maximum yield reached but has problems in that (a) the control operation of the temperature and the pressure throughout the reaction time is very complicated so that hardly no reproducibility of the results can be expected from the standpoint of practice, (b) practical difficulty is involved in the control of the rate of continuous introduction of the diamine in balance with the amount distilled out, and (c) re-use of the distilled and recycled diamine as a reactant in the reaction is not recommendable because of the variety in the by-products contained therein bringing about a problem of waste disposal. This method is also disadvantaged by the difficulty when modification to a continuous process is intended because of the necessity of the complicated control operation during several hours of the reaction.

Thus very strict control of the parameters in the reaction is required in the prior art with complicated control operation in order to attain high yield of the objective compound because of the extremely low reaction velocity of the imidazolination reaction itself necessitating a batch-wise operation in carrying out the reaction.

SUMMARY OF THE INVENTION

An object of the present invention is therefore to provide a novel and effective method for the preparation of imidazoline compounds of high quality in a high yield or, in particular, a method in which high-quality imidazoline compounds with low acid value as well as low coloration can be obtained in a high yield by way of a continuous operation of the reaction free from the above described problems in the prior art.

The method of the invention, completed as a result of the extensive investigations undertaken by the inventors, comprises introducing continuously a diamine and a higher fatty acid into a substantially vertical reaction column having a packed zone maintained at a specifically chosen temperature and inner pressure to give at least 10 minutes of the staying time of the reactants in the zone.

In further detail, the method of the invention for the preparation of imidazoline compounds comprises intruducing continuously a mixture of a diamine represented by the general formula $$H_2N-CH_2CH_2-NHR', \qquad (I)$$

where R' is an alkylol group with 2 to 4 carbon atoms, and a higher fatty acid represented by the general formula $$RCOOH, \qquad (II)$$

where R is an alkyl or an alkenyl group with 8 or more of carbon atoms, into the upper part of the packed zone of a reaction column kept at a temperature of 180° to 250° C. under a pressure of 40 to 70 mmHg, removing the condensation water produced by the condensation reaction of the diamine and the fatty acid distilled out of the column while the diamine distilled out is refluxed into the reaction zone, and taking out the reaction mixture continuously from a reservoir vessel installed below the packed zone, the rates of introducing the mixture of the diamine and the fatty acid and taking out the reaction mixture being such that the mean staying time of the reaction mixture in the packed zone is at least 10 minutes.

In accordance with the above described inventive method, an imidazoline compound represented by the general formula

with a remarkably lower acid value and coloration than in the prior art methods can be produced with high productivity.

The method of the invention is especially suitable for the preparation of the imidazoline compounds where the group R' is a hydroxyethyl group, viz. 1-hydroxyethyl-2-(higher alkyl or alkenyl)-imidazolines.

BRIEF DESCRIPTION OF THE DRAWING

The FIGURE is a schematic showing of the flow diagram suitable for carrying out the method of the present invention in which:

1 is a reaction column filled with packings;
2 is a condenser;
3 is a reservoir vessel; and
4 is an inlet tube for the starting reactants.

DETAILED DESCRIPTION OF THE PREFERRED EMBODIMENTS

One of the starting reactants in the inventive method is a diamine represented by the general formula (I) above, in which the group represented by the symbol R' is an alkylol group with 2 to 4 carbon atoms, viz. $-C_2H_4OH$, $-C_3H_6OH$ or $-C_4H_9OH$. Accordingly, the diamine compound is exemplified by $NH_2C_2H_4NHC_2H_4OH$, $NH_2C_2H_4NHC_3H_6OH$ and $NH_2C_2H_4NHC_4H_9OH$. They are not necessarily of special grades or purity but commercially available ones may be used as such.

The higher fatty acid as the reactant on the other side has at least 8 carbon atoms in a molecule and is exemplified by caprylic acid, capric acid, lauric acid, myristic acid, palmitic acid, stearic acid and oleic acid as well as those fatty acid mixtures derived from coconut oil, beef tallow and the like rich in lauric acid or stearic acid.

The molar ratio of the diamine to the fatty acid introduced into the reaction column is preferably such that the diamine is slightly in excess over the stoichiometric amount, say, 1.01:1 or higher or, more preferably, 1.05:1 or higher of the diamine to fatty acid ratio. The upper limit in this ratio is not so critical but is determined largely by the economical reason as well as the purity of the obtained product. For example, even a large excess of the diamine, say, 2 to 3 moles of the diamine per mole of the fatty acid, has no adverse effect on the reaction velocity but is not recommended from the economical standpoint of view and the purity of the product containing considerable amount of the unreacted diamine. In this respect, the ratio is preferably below 1.30:1 or, more preferably, below 1.10:1. When the ratio exceeds 1.10:1, a disadvantage is caused in removing the diamine from the reaction product by distillation.

The method of the present invention is now described with reference to the schematic flow diagram shown in the drawing. In the FIGURE, 1 is a reaction column with a length filled with packings in the zone indicated by hatching to form a packed zone. The packings are naturally made of a material with sufficient heat resistance and corrosion resistance and the shape of the packings is, though not limitative, desirably such that sufficiently large surface area is provided as in McMahon packings, Raschig rings, spherical packings and the like. The reaction column 1 is provided with a heating means outside the column over the length of the column to ensure the desired temperature inside the column. 2 is a fractional condenser and 3 is a reservoir vessel with heating means.

The reactants, i.e. the diamine and the higher fatty acid, are, separately or as a mixture, introduced into the upper part of the reaction column, preferably, at a constant rate through the inlet tube 4. The mixture of the diamine and the fatty acid introuduced into the reaction column descends in the column while spreading over the surfaces of the packings where it is heated and well mixed to effect the imidazolination reaction. The condensation water produced by the condensation reaction evaporates together with part of the diamine to leave the reaction column 1 at the top from where the vapor reaches the condenser 2 through the conduit 5. The diamine contained in the vapor is fractionally condensed in the condenser and the remaining water vapor is discharged out through the conduit 7. The diamine condensed in the condenser is refluxed into the column 1 through the conduit 6. It is recommended that the coolant running through the condenser is warmed at a temperature of 40° to 80° C. in order to obtain clear-cut fractional condensation of the diamine.

The temperature inside the reaction column 1 should be strictly controlled within a range of 180° to 250° C. in order to ensure the production of a high-quality imidazoline compound of the object in high efficiency. This is because that the velocity of the imidazolination reaction is low at a temperature lower than 180° C. with an unsatisfactory result in the maximum yield of the objective product while a temperature higher than 250° C. results in the coloration and unpleasant smelling of the reaction product due to the undesirable thermal decomposition or oxidation of the reactants. In order to avoid this undesirable thermal decomposition or oxidation of the reactants as well as the reaction product, it is a recommendable way that the atmosphere in the reaction column is kept inert with an inert gas such as nitrogen although the necessity is relatively small in the method of the invention according to which the pressure inside the reaction column is reduced to 40 to 70 mmHg as described below.

The pressure inside the column 1 is preferably maintained at 40 to 70 mmHg. When the pressure is lower than 40 mmHg, the evaporation of the diamine is so vigorous that satisfactory mixing of the diamine with the higher fatty acid can hardly be expected leading to an unsatisfactory maximum yield of the product as a natural consequence while, on the other hand, the progress of the reaction is disturbed under a pressure higher than 70 mmHg because of the insufficient removal of the condensation water by distillation.

It is desirable that the reaction mixture of the diamine and the higher fatty acid stays in the column 1 at least 10 minutes to obtain a satisfactorily high yield of the objective product. It is of course that the staying time can be varied as a function of several parameters such as the column volume, column height, shapes of the packings and the like.

The reaction mixture, having left the column 1 at the bottom after descending within the column, is collected in the reservoir vessel 3 kept at the same temperature as the packed zone in the column by use of the heating means to effect the evaporation of the water droplets formed by fractional condensation and coming down with the reaction mixture and the condensation water not evaporated and contained as formed in the reaction mixture. An additional advantage obtained by the reservoir vessel is that the vapor evolved in the reservoir vessel and entering the column is effective in supplying heat energy into the column to ensure more uniform temperature distribution throughout the column. After staying in the reservoir vessel for certain length of time, say, 30 minutes or so, to be sufficient to give the above effects, the reaction mixture is discharged out of the vessel at the bottom continuously through the conduit 8.

The heating means of the reaction column 1 and the reservoir vessel is not limitative and may be an electric heater or a heat transfer medium.

It is optional that, instead of refluxing the evaporated diamine by condensation in the condenser 2, a fresh portion of the diamine is introduced into the column 1 through the conduit 6 at a rate equal to the evaporation of the same diamine in the column.

Although not well understood for the moment, the mechanism is presumably as undermentioned for the remarkable improvement obtained by the present invention establishing the continuous production of the imidazoline compounds with much shorter staying time of the reaction mixture in the reaction zone than in conventional batch-wise process taking several hours of the reaction time. Firstly, the evaporation rate of the condensation water from the reaction mixture is increased beyond comparison owing to the much increased surface area of the reaction mixture because the reaction mixture descends in the column while spreading as a thin film over the surface of the packings. Secondly, a gas-liquid equilibrium is established between the diamine or condensation water contained in the liquid reaction mixture and the gaseous diamine or condensation water in the vapor phase so that the evaporation of the diamine is retarded with further acceleration of the evaporation of the condensation water. Possibly, a combination of the above two mechanisms is the ground for the surprising improvement in the reaction velocity attained by the present invention.

Thus the method of the present invention enables the continuous production of the imidazoline compounds undertaken with great difficulties in the prior art. The method is also suitable for the manufacture of the imidazoline compounds in an industrial scale owing to the simplicity in the operation in comparison with the conventional methods.

It should be noted that the content of the objective imidazoline compound in the discharged reaction mixture can be as high as 95% by weight or higher with an appropriate molar ratio of the diamine and the higher fatty acid close to 1 in the starting reaction mixture. Therefore the reaction mixture obtained in the reaction may be used as such as an imidazoline compound of sufficiently high purity without further treatment or purification in various applications.

Following are the Example and the Control for comparative purpose to explain the method of the present invention in further detail.

EXAMPLE

The flow diagram in this experiment was the same as in the drawing annexed and a glass cylinder of 18 mm inner diameter and 400 mm length was used as the reaction column 1 packed over a length of about 380 mm with meshed McMahon packings each with a dimension of about 7 mm. A nichrome wire was wound around the column 1 over the whole length to provide an electric heating means. Water warmed at 50° C. was run through the condenser 2. The reservoir vessel 3 was a 200 ml-capacity glass flask equipped with a thermometer and a discharge conduit 8 at the bottom and wrapped evenly with an electric heater.

Into the reaction column thus prepared was introduced a mixture of coconut oil fatty acid with an average molecular weight of 207 and aminoethylethanolamine with the molecular weight of 104 in a molar ratio as indicated in Table I to follow through the inlet tube 4 connected at the upper part of the column at a rate also indicated in the table. The reaction was performed with varied temperatures and pressures as the parameters of the reaction conditions by careful control of the heating means and vacuum pump to produce reaction mixtures containing the objective imidazoline compound as the product. The mean staying time of the reaction mixture in the reaction column was calculated by taking the amount of the hold-up as equal to 4 g as the basis in order to avoid the difficulty in direct measurement.

The reaction mixture collected in the reservoir vessel 3 was continuously discharged out of the vessel through the conduit 8 at such a rate that the staying time of the reaction mixture in the vessel was about 30 minutes in an average. The reaction conditions and the properties of the thus obtained reaction products are summarized in the table.

In the table, the values of "Mean staying time", "Condensation water distilled out" and "Coloration" were calculated or measured according to the following standards.

Mean staying time: calculated with the following equation assuming that the hold-up amount of the reactants in the column was 4 g.

$$\text{Mean staying time, minutes} = \frac{4}{\text{Feeding rate of the reactants, g/hour}} \times 60$$

Condensation water distilled out: the percentage of the water distilled out of the column to the theoretical amount equal to 2 moles of water per mole of the fatty acid.

Coloration: determined absorption-spectrophotometrically for a 10% ethanol solution of the sample in a Model 139 HITACHI spectorophotometer at a wavelength of 420 nm with the slit width adjusted to 0.05 mm and expressed in $(-\log T) \times 10^3$ where T is the absorbance as measured.

Table I

| Experiment No. | | Diamine/fatty acid molar ratio | Mean staying time, minutes | Temperature °C. | Pressure, mmHg | Condensation water distilled out, % | Reaction Product Acid value | coloration |
|---|---|---|---|---|---|---|---|---|
| Present Invention | 1 | 1.02:1 | 18 | 240 | 55 | 97 | 2.5 | 370 |
| | 2 | 1.05:1 | 12 | 230 | 60 | 98 | 2.0 | 290 |
| | 3 | 1.05:1 | 16 | 240 | 60 | 99 | 1.1 | 400 |
| | 4 | 1.05:1 | 23 | 240 | 55 | 99 | 1.0 | 440 |
| | 5 | 1.25:1 | 16 | 250 | 60 | 100 | 0.9 | 500 |
| | 6 | 1.25:1 | 16 | 200 | 55 | 98 | 2.0 | 240 |
| | 7 | 1.25:1 | 25 | 200 | 55 | 98 | 1.8 | 290 |
| | 8 | 2.00:1 | 10 | 200 | 55 | 96 | 2.8 | 200 |
| Control | 9 | 1.05:1 | 7 | 250 | 55 | 89 | 10.0 | 370 |
| | 10 | 1.25:1 | 6 | 250 | 40 | 91 | 8.3 | 400 |
| | 11 | 1.25:1 | 12 | 270 | 60 | 100 | 0.8 | 900 |
| | 12 | 1.25:1 | 16 | 170 | 55 | 93 | 7.0 | 200 |

An imidazoline compound used in most of the applications has desirably an acid value of 3.0 or below and a coloration of 500 or below. In this connection, Experiments No. 9 to No. 12 are apparently unsatisfactory, among which products with higher acid values were obtained in Experiments No. 9 and No. 10 with shorter staying time of the reaciton mixture in the reaction column, a product with a higher acid value was obtained in Experiment No. 12 with lower reaction temperature and a product with a low acid value but intense coloration was obtained in Experiment No. 11 with higher reaction temperature. Thus the reaction conditions established in the present invention are very critical and no satisfactory results can be expected with the reaction conditions outside the range in the present invention. On the other side, reaction products with satisfactorily low acid values and coloration were obtained in Experiments No. 1 through No. 8 in accordance with the method of the present invention.

COMPARATIVE EXAMPLE

A batch-wise reaction was undertaken with the same coconut oil fatty acid and the same aminoethylethanolamine as in the preceding Example. Into a flask equipped with a stirrer and a reflux condenser and connected to a vacuum pump was introduced 207 g of the coconut oil fatty acid which was heated to about 80° C. under agitation and the pressure was reduced to 45 mmHg by driving the vacuum pump. The aminoethylethanolamine in an amount of 109 g was admixed to the coconut oil fatty acid in the flask, the molar ratio of the diamine and the fatty acid being 1.05:1, and the temperature of the reaction mixture was further increased while water at 50° C. was run through the reflux condenser.

The reaction started when the temperature of the reaction mixture in the flask reached about 140° C. with condensation of the vapor in the reflux condenser. The condensate was, however, the diamine alone which refluxed to the reaction flask and the uncondensed water vapor was led to cold trap at 0° C. cooled with ice-water where it was condensed. The temperature of the reaction mixture was gradually incresed from 140° C. at the beginning of the reaction up to 200° C. after 6 hours of the reaction where the heating was stopped and the reaction mixture was cooled down to 50° C. to be taken out of the reaction flask.

The same batch-wise experimental procedure was repeated except that the amount of aminoethylethanolamine was increased to 130 g instead of 109 g giving the molar ratio of the diamine to fatty acid equal to 1.25:1. The properties of the reaction products obtained in these batch-wise experiments are set out in Table II below.

Table II

| Experiment No. | Diamine/fatty acid molar ratio | Condensation water distilled out, % of the theoretical amount | Acid value | Coloration |
|---|---|---|---|---|
| 1 | 1.05:1 | 96 | 5.2 | 480 |
| 2 | 1.25:1 | 99 | 1.6 | 520 |

In spite of the lengthy reaction time, the experiments resulted in either too high acid value in Experiment No. 1 with the diamine to fatty acid molar ratio of 1.05:1 or intense coloration in Experiment No. 2 with the ratio equal to 1.25:1.

What is claimed is:

1. A method for the preparation of an imidazoline compound represented by the general formula

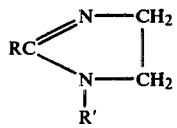

where R is an alkyl group having at least 8 carbon atoms and R' is an alkylol group having 2 to 4 carbon atoms, which comprises the steps of
   (a) supplying continuously, either separately or as a mixture, a fatty acid represented by the general formula RCOOH and an N-substituted ethylenediamine represented by the general formula $H_2N$—$CH_2CH_2$—$NHR'$, where R and R' have the same meaning as defined above, into the upper part of a reaction column kept at a temperature in the range from 180° to 250° C. under a pressure of 40 to 70 mmHg,
   (b) removing the water formed in the reaction column by the condensation reaction of the N-substituted ethylenediamine and the fatty acid with simultaneous refluxing of the N-substituted ethylenediamine with a reflux condenser cooled to about 40° to 80° C., and
   (c) discharging continuously the reaction mixture from a reservoir vessel maintained at about 180° to 250° C. and installed below the reaction column at such a rate that the residence time of the reaction mixture in the reaction column is at least 10 minutes and the residence time of the reaction mixture in the reservoir vessel is at least about 30 minutes.

2. The method as claimed in claim 1 wherein the molar ratio of the N-substituted ethylenediamine to the fatty acid is in the range of from 1.01:1 to 1.30:1.

3. The method as claimed in claim 1 wherein the reaction column is packed with packings.

4. The method as claimed in claim 1 wherein the N-substituted ethylenediamine is aminoethylethanolamine.

* * * * *